(12) United States Patent
Brox et al.

(10) Patent No.: US 6,555,132 B1
(45) Date of Patent: *Apr. 29, 2003

(54) SOFT GELATIN CAPSULE MANUFACTURE

(75) Inventors: Werner Brox, Beerfelden (DE); Armin Meinzer, Freiburg (DE); Horst Zande, Schönbrun (DE)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/690,401

(22) Filed: Oct. 17, 2000

Related U.S. Application Data

(63) Continuation of application No. 09/329,125, filed on Jun. 9, 1999, now abandoned, which is a continuation of application No. 08/841,734, filed on Apr. 29, 1997, now Pat. No. 5,985,321, which is a continuation of application No. 08/312,251, filed on Sep. 26, 1994, now abandoned.

(30) Foreign Application Priority Data

Sep. 28, 1993 (DE) ............................................. 43 32 931

(51) Int. Cl.[7] ............................ A61K 9/48; A61K 9/66; A61K 38/13
(52) U.S. Cl. ........................ 424/451; 424/452; 424/455; 424/456; 424/458; 514/183; 514/291
(58) Field of Search .................................. 424/451, 452, 424/455, 456, 458; 514/183, 291

(56) References Cited

U.S. PATENT DOCUMENTS

| | | |
|---|---|---|
| 4,067,960 A | 1/1978 | Fadda |
| 4,088,750 A | 5/1978 | Cresswell et al. |
| 4,198,391 A | 4/1980 | Grainger |
| 4,388,307 A | 6/1983 | Cavanak |

(List continued on next page.)

FOREIGN PATENT DOCUMENTS

| | | |
|---|---|---|
| CA | 1 211 712 | 9/1986 |
| EP | 0121321 | 10/1984 |
| EP | 0 240 581 | 10/1987 |
| EP | 257386 | 3/1988 |
| EP | 539319 | 4/1993 |
| GB | 1 484 411 | 9/1977 |
| GB | 1 508 770 | 4/1978 |
| GB | 2209671 | 5/1989 |
| GB | 2257359 | 1/1993 |
| JP | 62/207460 | 9/1987 |
| JP | 63/309264 | 12/1988 |
| WO | 8403417 | 9/1984 |
| WO | 8907936 | 9/1989 |
| WO | WO 94/05312 | 3/1994 |

OTHER PUBLICATIONS

European Search Report EP 94 11 5081.
Search Report Application No. GB 9419353.9.
Journal of Pharmaceutical Sciences Jan. 1986, vol. 75, No. 1 (pp. 62–64).
Remington's Pharmaceutical Sicences, 16th Ed. (1980), Chapter 89, p. 1580.
Merck Index, 11th Edition, p. 1247, entry No. 7868 for propylene gylcol, (1989).

(List continued on next page.)

Primary Examiner—Michael G. Hartley
Assistant Examiner—M. Haghighatian
(74) Attorney, Agent, or Firm—John D. Thallemer

(57) ABSTRACT

Soft gelatin capsules having a capsule shell comprising gelatin, plasticizers and, if desired or required, further auxiliary agents, and a capsule filling containing a solvent including a migrateable solvent such as 1,2-propyleneglycol as a solvent in the capsule filling and in the capsule shell. The manufacture of said capsules is improved, if in the process for making the soft gelatin capsules the gelatin bands are cooled with a liquid, and preferably with water.

33 Claims, 1 Drawing Sheet

U.S. PATENT DOCUMENTS

| | | | |
|---|---|---|---|
| 4,695,450 A | 9/1987 | Bauer et al. | 424/456 |
| 4,713,246 A | 12/1987 | Begum et al. | 424/455 |
| 4,719,239 A | 1/1988 | Muller et al. | 514/785 |
| 4,744,988 A | 5/1988 | Brox | |
| 4,780,316 A | 10/1988 | Brox | 424/455 |
| 4,804,542 A | 2/1989 | Fischer et al. | 424/456 |
| 4,817,367 A | 4/1989 | Ishikawa et al. | |
| 4,829,057 A | 5/1989 | Brox et al. | |
| 4,888,239 A | 12/1989 | Brox | |
| 4,891,229 A | 1/1990 | Brox et al. | |
| 4,892,766 A | 1/1990 | Jones | 428/36.4 |
| 4,927,638 A | 5/1990 | Bykadi et al. | 424/455 |
| 4,935,293 A | 6/1990 | Borkan et al. | 424/455 |
| 4,990,337 A | 2/1991 | Kurihara et al. | |
| 5,178,877 A | 1/1993 | Garren et al. | 424/455 |
| 5,200,191 A | 4/1993 | Steele et al. | 424/453 |
| 5,206,219 A | 4/1993 | Desai | 424/455 |
| 5,254,294 A | 10/1993 | Wunderlich | |
| 5,342,625 A | 8/1994 | Hauer et al. | 424/455 |
| 5,376,381 A | 12/1994 | Weiner et al. | 424/455 |
| 5,376,688 A | 12/1994 | Morton et al. | 514/786 |
| 5,385,737 A | 1/1995 | Shigeno et al. | 424/451 |
| 5,431,916 A | 7/1995 | White | 424/455 |
| 5,456,746 A | 10/1995 | Kokubun et al. | 106/131 |
| 5,505,961 A | 4/1996 | Shelley et al. | 424/451 |
| 5,532,002 A | 7/1996 | Story | 424/456 |
| 5,543,393 A | 8/1996 | Kim et al. | 514/11 |
| 5,614,217 A | 3/1997 | Chiprich et al. | 424/451 |
| 5,626,872 A | 5/1997 | Vasquez | 424/451 |
| 5,641,512 A | 6/1997 | Cimiluca | 424/455 |
| 5,665,772 A * | 9/1997 | Cottens et al. | 514/514 |
| 5,725,878 A | 3/1998 | Al-Razzak et al. | 424/456 |
| 5,738,871 A | 4/1998 | Story | 424/451 |
| 5,798,333 A | 8/1998 | Sherman | 514/11 |
| 5,932,243 A | 8/1999 | Fricker et al. | 424/450 |
| 5,958,876 A | 9/1999 | Woo | 514/11 |
| 5,985,321 A * | 11/1999 | Brox et al. | 424/451 |
| 6,239,124 B1 * | 5/2001 | Zenke et al. | 514/183 |

OTHER PUBLICATIONS

The Theory and Practice of Industrial Pharmacy, ed. Lachman, et al., 2nd Edition (Lea & Febiger 1976), pp. 404–420.

The Theory and Practice of Industrial Pharmacy, Lachman et al., 3rd ed., (1986), pp. 400–407.

Abstract of JP56130219 (1981).

Lachman et al., The Theory and Practice of Industrial Pharmacy, $3^{rd}$ Edition, "Soft Gelatin Capsules", pp. 398–412 (1986).

Shah et al., "Elasticity of Soft Gelatin Capsules Containing Polyethylene Glycol 400–Quantitation and Resolution", Pharmaceutical Technology, pp. 126–131 (1992).

Digenis et al., "Cross–Linking of Gelatin Capsules and Its Relevance to Their In Vitro–In Vivo Performance", J. Pharm. Sci., vol. 83, No. 7, pp. 915–921 (1994).

Prince, "Microemulsions", Emulsions and Emulsion Technology, Chapter 3, New York, Part 1, pp. 125–177 (1974).

Prince, "The Mixed Film Theory", Academic Press, New York, pp. 91–129 (1977).

Hom et al., "Softgels". See letter from Cavelier Abogados, dated Nov. 27, 2001.

Georgakopoulos et al., "Oral Anhydrous Non Ionic Microemulsions Administrated in Softgel Capsules", Gattefossé, pp. 11–20 (1992–1993).

Reich, "Action and Optimization of Plasticizers in Soft Gelatin Capsules", Pharm. Ind., vol. 56, No. 10, pp. 915–920 (1994).

Sucker et al., Pharmazeutische Technologie, Ed. Georg Thieme Verlag Stuttgart , p. 469 (1978).

Hom et al., "Theophylline Sustained Release Softgels", J. Pharm. Sci., vol. 76, No. 11, p. S297 (1987).

Jimerson, "Soft Gelatin Capsule Update", Drug Development and Industrial Pharmacy, vol. 12, Nos. 8 & 9, pp. 1133–1144 (1986).

Wilkinson et al., "Softgels: Manufacturing Considerations", Drugs and the Pharmaceutical Sciences, vol. 41, Chapter 10, pp. 409–449 (1990).

Shiseido Co. Ltd, Derwent Abstracts, 92–231881/28 (JP04159218–A—Jun. 2, 1992).

Nippon Med. Service (Yamo–), Derwent Abstracts, 90–302773/40 (JP 2215–466–A–Aug. 26, 1990).

* cited by examiner

SOFT GELATIN CAPSULE MANUFACTURE

This is a continuation of U.S. patent application Ser. No. 09/329,125 filed Jun. 9, 1999, now abandoned, which is a continuation of U.S. application Ser. No. 08/541,734 now U.S. Pat. No. 5,985,321, filed Apr. 29, 1997, which is a continuation of U.S. patent application Ser. No. 08/312,251, filed Sep. 26, 1994, now abandoned.

The present invention relates to soft gelatin capsules having a capsule shell made of gelatin, plasticizing agents, in particular 1,2-propylene glycol, and optionally further auxiliary materials, and a capsule filling containing solvent, adjuvants and one or more pharmacologically active substances. The invention further relates to a process for preparing such soft gelatin capsules.

Some pharmacologically active substances may have biopharmaceutical and/or physicochemical properties which make them difficult to formulate into commercially acceptable formulations. Such substances may however be conveniently administered in liquid form, e.g. in a complex carrier medium made up of several components. Solvents such as 1,2-propylene glycol and dimethyl isosorbide have great potential in such carrier media. The carrier medium may be designed to form an emulsion in the stomach thereby facilitating absorption of the pharmacologically active substance. The carrier medium may have to be accurately prepared and even slight variations in the composition cannot be tolerated without irreversibly upsetting the system, and destroying its beneficial properties. Thus the solubilizing properties of the capsule filling may be changed and the active substance precipitates out. This precipitation process may be irreversible, and the patient is under-dosed. The emulsifying properties of the capsule filling may be changed, and, upon administration, an emulsion may not be formed in the stomach and the pharmacologically active substance is not correctly or reproducibly absorbed.

Encapsulation of such liquid formulations in soft gelatine capsules potentially offers a very convenient way of administering such pharmacologically active substances. However the manufacture of commercially acceptable liquid filled soft gelatine capsules is fraught with difficulties which restricts the availability of this approach. Thus, during manufacture, the capsule shell is formed from wet gelatine bands and the resultant wet capsules are dried. During this stage or even afterwards, we have found that components in the capsule filling may migrate into the capsule shell, and vice versa, thereby changing the composition of the capsule filling at least in the boundary region near the interface of the capsule filling and the capsule shell, with the result that the beneficial properties of the capsule filling are lost.

In recent years microemulsion pre-concentrates have been developed as carrier media for active substances which are sparingly soluble in water, which microemulsion pre-concentrates exhibit a distinct improvement in the bioavailability. Examples of such microemulsion pre-concentrates have been described, for example, in the UK patent application No 2 222 770 A (equivalent to DE-A-39 30 928) for the active substance cyclosporin. Microemulsion pre-concentrates consist of a hydrophilic phase, a lipophilic phase and a surface-active agent. As the hydrophilic phase there has been expressly mentioned and also used in the examples propyleneglycol, and more specifically 1,2-propylene-glycol. UK patent application No 2 222 770 A mentions, as an application form of the microemulsion pre-concentrates in addition to hard gelatin capsules, also soft gelatin capsules as well as other parenteral or topically applicable forms; cf. page 13, lines 16–25. We have found that microemulsion pre-concentrates comprising 1,2-propyleneglycol as the hydrophilic phase in soft gelatin capsules are prone to the migration of the 1,2-propyleneglycol into the capsule shell from the capsule filling. Not only softening of the capsule shell occurred, but also a destruction of the microemulsion pre-concentrates, because the hydrophilic component was withdrawn therefrom.

Since propyleneglycol, and more specifically 1,2-propyleneglycol, is a good hydrophilic solvent, it would be desirable to employ this solvent also for the preparation of capsule fillings. It is true, it is readily possible to produce such gelatin capsules wherein, for example, glycerol or sorbitol are used as the plasticizer for the capsule shell. However, such soft gelatin capsules are not stable, since with the lapse of time the propyleneglycol migrates into the capsule shell from the capsule filling so that the capsules will become weak.

Furthermore, such softened capsules will undergo deformation, because due to the migration of part of the solvent into the capsule shell from the capsule filling there will be a decrease in volume and a reduction in pressure in the interior of the capsule.

We have now found that the migration of, e.g. 1,2-propyleneglycol, may be hindered by using this component in the gelatine band composition with the result that it is present in the capsule shell. However we also experienced difficulties in the commercial manufacture of soft gelatine capsules containing 1,2,propylene glycol.

In EP-B-0 121 321 there have been disclosed soft gelatin capsules wherein at least one pharmacologically active substance has been dissolved or suspended in a liquid polyethyleneglycol, the capsule comprising gelatin, a plasticizer therefor and a compound for preventing embrittlement which compound is a mixture comprising sorbitol and at least one sorbitan. If so desired, alcohols having several hydroxyl groups are added to the capsule shell as the embrittlement-preventing compound. As polyhydric alcohols suitable for this purpose there have been mentioned glycerol, sorbitol and propyleneglycol. Furthermore this patent specification mentions that the capsule filling may also contain such alcohols comprising several hydroxyl groups. Again glycerol, sorbitol and propyleneglycol have been described. However, it is conspicuous that in the examples glycerol has been exclusively used for the capsule filling as well as for the capsule shell. This may be to the fact that the attempts to substitute propyleneglycol for glycerol in the capsule shell failed. Although propyleneglycol is basically suitable as a plasticizer for gelatin, in the large scale commercial manufacture of such soft gelatin capsules according to the so-called Rotary Die Process the gelatin bands, once poured onto the cooling drums, may be removed only with difficulty from the cooling drums and passed to the molding rolls where the encapsulation is effected. The reason therefor is that the gelatin bands containing propyleneglycol as the plasticizer are substantially more tacky than those containing glycerol or sorbitol as the plasticizer. This is why soft gelatin capsules having a capsule shell comprising gelatin and propyleneglycol as a plasticizer have never been introduced into practice.

In EP-B-0 257 386 there have been disclosed gelatin capsules which, in the capsule filling, contain a solvent mixture which contains at least 5% by weight of ethanol and at least 20% by weight of one or more partial glycerides of fatty acids having from 6 to 18 carbon atoms. In the description there has been mentioned that the capsule shell may contain glycerol, propyleneglycol, sorbitol and sorbitans as the plasticizer. However, again just glycerol, sorbitol and sorbitans were used in the capsule shell, because propylene glycol results in the above-described undesirable tackiness.

Since the use as a plasticizer of propyleneglycol in the capsule shell results in difficulties in the manufacture of soft gelatin capsules according to the Rotary Die Process, there was a further need for developing a process wherein the manufacture of soft gelatin capsules according to the Rotary Die Process is possible even in the case where the capsule shell contains a component which leads to tackiness, e.g. 1,2-propyleneglycol.

We have found surprisingly by cooling the cooling drum with a liquid coolant it is possible to eliminate—or at least to suppress—the troublesome tackiness observed, and a commercially feasible manufacture of such soft gelatin capsules is possible.

Therefore, the present invention provides soft gelatin capsules which include a capsule shell comprising gelatin, plasticizers and, if desired or required, further auxiliary materials, and a capsule filling containing solvent, adjuvants and one or more pharmacologically active substance(s), wherein the solvent of the capsule filling, at least in part, is a migrateable component and which, nevertheless, are stable.

Using the process according to the invention it is also possible to produce soft gelatin capsules according to EP-B-0 121 321 which contain liquid polyethyleneglycol in the capsule filling and 1,2-propyleneglycol in the shell.

In one aspect the invention provides a liquid filled soft gelatin capsule characterized in that the capsule shell contains a migrateable component (other than glycerol) which is also present in the capsule filling.

In another aspect the present invention provides a process for encapsulating a liquid mixture in gelatine to form soft gelatine capsules, wherein one component of the mixture has a propensity to migrate into gelatine, characterized in that the gelatine composition used in the encapsulation process contains also the said migrateable component, and said migrateable component is other than glycerol.

In another aspect the present invention provides a process for manufacturing soft gelatin capsules having a capsule shell comprising gelatin and a component which leads to tackiness, characterized in that cooling of the gelatin bands to form the capsule shell is effected using a liquid coolant. Preferably, but not necessarily, the component which leads to tackiness is a migrateable component.

Typical migrateable components include non-volatile pharmaceutically acceptable solvents which are capable of mixing with, or forming a solid solution with, the gelatine. As mentioned above glycerol is mentioned in the above EP-B-0-121321. However, glycerol is not a particularly good solvent, and in general does not lead to tackiness. Glycerol may of course also be present as described hereinafter.

Typical migrateable solvents include tetrahyrofurylalcohol ethers, e.g. glycofurol diethylene glycol mono ethyl ether, e.g. transcutol, 1,3-dimethyl-2-imidazolidinone, dimethylisosorbide, polyethylene glycol (e.g. of molecular weight from 200 to 600) and preferably propylene glycol or solvents having similar migration capability. Preferably, the concentration of the migrateable component in the capsule shell is chosen to be so high that an approximately stable equilibrium of the concentrations between the capsule shell and the capsule filling is established soon after encapsulation. During the equilibration phase the migrateable component may migrate from the capsule shell into the capsule filling (thereby increasing its concentration in the capsule filling and decreasing it in the gelatine shell), but migration of the migrateable component into the capsule shell from the capsule filling is significantly reduced.

In one embodiment of the invention the carrier filling at least partially is 1,2-propyleneglycol, but not predominantly polyethyleneglycol. In another aspect the present invention accordingly provides a soft gelatin capsule having a capsule shell comprising gelatin, plasticizers and, if desired or required, further auxiliary agents, and a capsule filling containing a solvent, wherein the solvent at least partially is 1,2-propyleneglycol, but not predominantly polyethyleneglycol, characterized in that the capsule shell contains 1,2-propyleneglycol.

The term gelatin as used herein includes not only unmodified gelatin as in the European Pharmacopeia and NF but also modified gelatin such as succinated gelatin.

Typical pharmacologically active substances include substances difficultly soluble in water, which have a solubility in water of less than 1% (w/v) such as cyclosporins and macrolides. Cyclosporins comprise a class of structurally distinct, cyclic, poly-N-methylated undecapeptides, generally possessing immunosuppressive, anti-inflammatory, anti-viral multidrug resistant and/or anti-parasitic activity, each to a greater or lesser degree. The first of the cyclosporins to be identified was the fungal metabolite Cyclosporin A, or Ciclosporin, and its structure is given in The Merck Index, 11th Edition; Merck & Co., Inc.; Rahway, N.J. USA (1989) under listing 2759. Large numbers of other cyclosporins are also known and examples are disclosed in UK patent application No 2 222 770 A. These include e.g. natural cyclosporins e.g. cycloporin A or G or synthetic cyclosporin derivatives thereof, e.g. ([3'-desoxy-3'-oxo-MeBmt]$^1$-[Val]$^2$-Ciclosporin) or [0-(2-hydroxyethyl)-(D) Ser]$^8$-Ciclosporin. Alternatively the pharmacologically active substance may be a macrolide such as a rapamycin, including derivatives thereof. Large numbers of derivatives of rapamycin have been synthesized, including for example those disclosed in U.S. Pat. Nos. 5,221,670 and 5,221,740, certain acyl and aminoacyl-rapamycins (see for example U.S. Pat. Nos. 4,316,885, 4,650,803, 5,151,413), and carbonates and amide esters (see for example EP 509795 and 515140) 27-desmethyl-rapamycin (see for example WO 92/14737), 26-dihydro-rapamycin (see for example U.S. Pat. No. 5,138,051), alkoxyester derivatives (see for example U.S. Pat. No. 5,233,036), and certain pyrazole derivatives (U.S. Pat. No. 5,164,399). A preferred rapamycin is 40-0-(2-hydroxy)ethyl rapamycin as disclosed in PCT/EP/93/02604.

FK 506 is a macrolide immunosuppressant that is produced by *Streptomyces tsukubaensis* No 9993. The structure of FK506 is given in the appendix to the Merck Index, as item A5. Also a large number of related compounds which retrain the basic structure and immunological properties of FK506 are also known. These compounds are described in a large number of publications, for example EP 184162, EP 315973, EP 323042, EP 423714, EP 427680, EP 465426, EP 474126, WO 91/13889, WO 91/19495, EP 484936, EP 532088, EP 532089, WO 93/5059 and the like. These compounds are termed collectively "FK506 compounds" in this specification. Examples of compounds are FK 506, ascomycin and those disclosed in EP 427 680, e.g. Example 66a. Other preferred compounds are disclosed in EP 465 426.

Any of the pharmacologically active substances mentioned in the specifications referred to above may be used in the capsules of the invention, e.g. in the examples mentioned hereinafter.

The carrier medium may contain a wide variety of components besides the migrateable component, e.g. as described hereinafter. It may, for example, contain a component which is volatile to some extent at the temperature of capsule production or storage such as ethanol which will to a certain extent pass through the capsule shell until equilibrium is reached.

The present invention is of particular importance for the manufacture of soft gelatin capsules in which the capsule filling may form an emulsion on mixing with water, see e.g. WO 94/5312. Thus the capsule filling may be a microemulsion pre-concentrate containing e.g. 1,2-propyleneglycol as the hydrophilic component e.g. those disclosed in UK patent application Nos 2 222 770 A and 2 257 359 A.

Other components may include a hydrophilic component, lipophilic component, surfactants and co-surfactants mixed together to provide a uniform mixture.

The capsule filling may contain a mixture of $C_{12-20}$ fatty acid mono-, di- and/or tri-glycerides e.g. from corn oil. Preferably the mono-, di-, and tri-glycerides have a low saturated fatty acid content preferably obtained from commercially available glycerol transesterification products by separation techniques as known in the art (for example purification to remove glycerol by washing and freezing procedures coupled with separation techniques such as centrifugation) to remove the saturated fatty acid components and enhance the unsaturated fatty acid component content. Typically the total saturated fatty acid component content will be less than 15%, (for example <10%, or <5%) by weight based on the total weight of the component. A reduction of the content of saturated fatty acid component in the mono-glyceride fraction may be observed after being subjected to the separation technique. A suitable process is described in WO 93/09211.

Because the undesirable migration into the capsule shell from the capsule filling is reduced, the amount of migrateable component to be used in the capsule shell depends on the desired initial and final concentrations of the migrateable component in the capsule filling. Thus, the content of migrateable component may be chosen so that the resulting concentration of migrateable component in the capsule shell after drying is from 2, e.g. 5, to 40% by weight. This may be accomplished by adding from 1 to 35% by weight of migrateable solvent to the gelatin composition. The gelatin composition initially contains water which in turn is removed in the subsequent drying operation.

A typical weight ratio of the migrateable component to gelatin is from 1:1 to 1:4.

The preferred range of the migrateable component content in the dried capsule shell is between 10 and 32%. In order to accomplish this, from 4 to 30% of migrateable component is added to the aqueous gelatin composition. Especially good results with microemulsion pre-concentrates containing 1,2-propyleneglycol as the hydrophilic component are achieved upon adding an amount of from 8 to 25% of migrateable component to the aqueous gelatin composition.

Another surprising advantage of the invention is that by using a migrateable component such as 1,2-propyleneglycol as the plasticizer in the capsule shell the amount of water required for dissolving and melting the gelatin may be reduced. While glycerol is highly viscous or syrupy and sorbitol itself even is a solid, the migrateable component such as 1,2-propyleneglycol may be a low-viscosity liquid. The reduction in the water content of the gelatin solution for producing the gelatin shell is a major advantage in that, during the process of drying the wet capsules, a smaller amount of water will make its way into the capsule filling from the initially moist shell. Thereby, with medicaments that are sparingly soluble in water, in many cases precipitation by crystallization of the active substance in the capsule filling can be prevented. Furthermore, due to the low diffusion of water into the capsule filling from the capsule shell a more stable capsule is obtained.

The capsule shell may of course additionally contain, as plasticizer in addition to the migrateable component, certain amounts of glycerol as well as conventional additives such as dyes, colorant pigments, flavoring agents, sugar, oligosaccharides or polysaccharides. However, it is preferred that the capsule shell in the wet state and, thus, at the time of encapsulation, contains sufficient migrateable component so that any migration of the migrateable component into the capsule shell from the capsule filling is reduced or prevented. The equilibrium concentration in the first place is determined by the concentration in the capsule filling of migrateable component such as propyleneglycol. However, it may also be affected by the qualitative and quantitative composition of the lipophilic component, the surfactants and the co-surfactants as well as the amount of further components of the capsule filling and the capsule shell. Thus, the optimum amount of migrateable component in the aqueous gelatin composition for an intended capsule filling can be determined by way of some simple and conventional preliminary tests.

If glycerol is employed as a further plasticizer in the capsule shell in combination with migrateable component, the concentration of the glycerol may be less than 18%, and preferably even below 12%, relative to the weight of the moist capsule shell. A typical weight ratio of the migrateable component to glycerol is from 1:1 to 1:0.2.

The process according to the invention is basically carried out in the same manner as usual in accordance with the Rotary Die Process as described in greater detail, inter alia, in Lachmann et al., "The Theory and Practice of Industrial Pharmacy", 2nd Edition, pages 404–419. It is apparent from FIG. 13-9 and its description in page 414, right column, last paragraph, that the gelatin band is passed over an air-dried rotating drum. The temperature of the cold air was reported to be 56° F. to 58° F., corresponding to 13.3° C. to 14.4° C., but this only inefficiently cools the gelatine.

BRIEF DESCRIPTION OF THE DRAWINGS

In the accompanying FIG. 1

Figure 1:
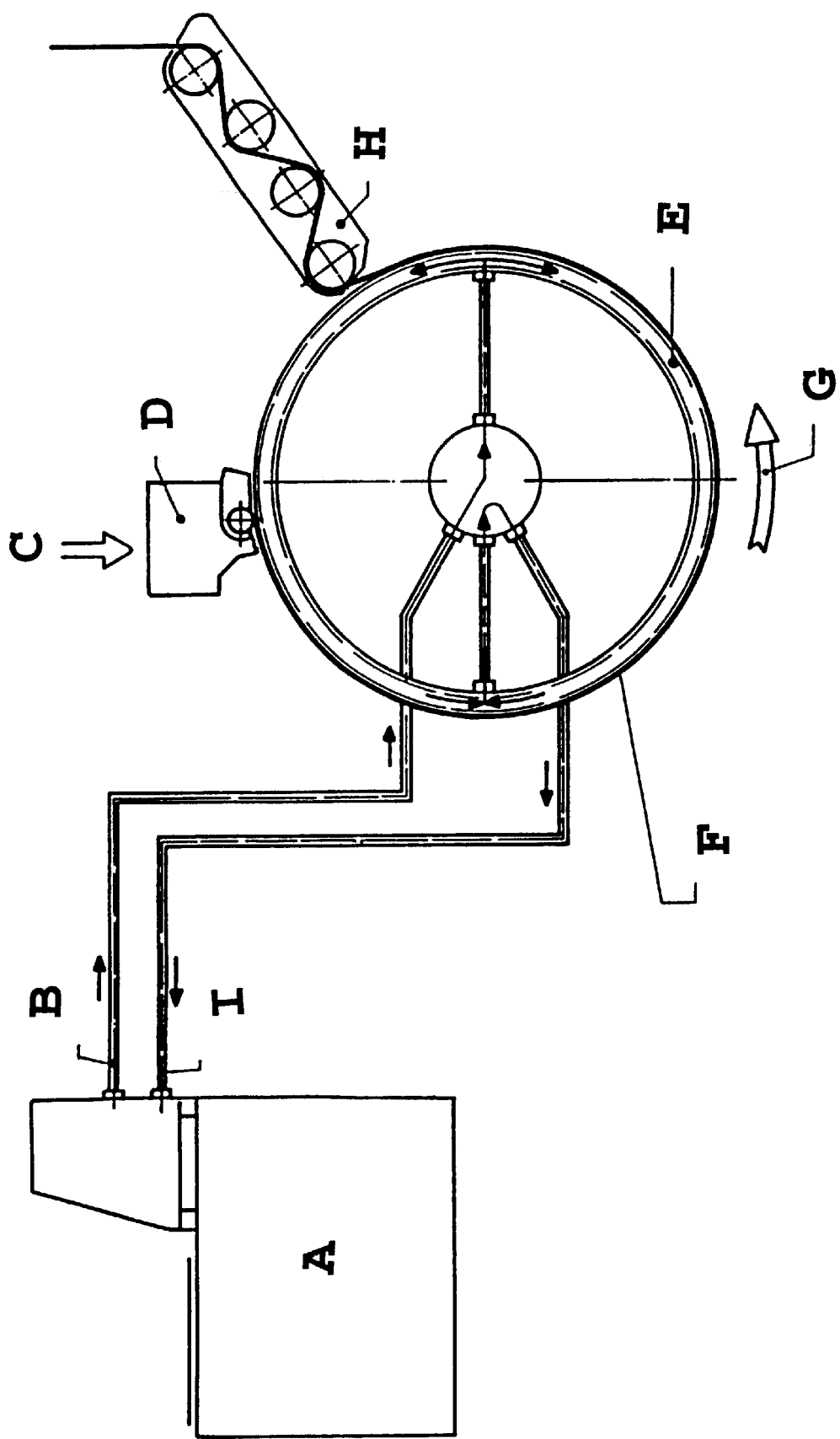

| | |
|---|---|
| A | represents a cooling apparatus for the cooling medium |
| B | shows the feed flow of the cooling medium |
| C | represents gelatine |
| D | represents the spreader box |
| E | represents the cooling drum |
| F | represents the gelatine band |
| G | indicates the direction of rotation of the cooling drum |
| H | represents the gelatine band take-off, and |
| I | shows the return flow of the spent cooling medium |

In another aspect the invention provides a cooling drum for cooling gelatin bands to form soft gelatine capsule shells wherein the drum is adapted with means for cooling the drum surface using a liquid coolant e.g. water. The cooling drum may be in association with a machine for producing soft gelatine capsules.

According to the invention, the cooling drum—as shown in the attached schematic figure—is cooled with a liquid coolant, with water being particularly preferred as the coolant, and being administered at such a rate that it can remove large quantities of heat quickly to provide a rapid and thorough cooling of the gelatin bands.

The gelatine bands conveniently have a temperature of about 65° C. when they contact the cooling drum. The bands may be better and more evenly cooled by the cooling drum according to the invention than an air-cooled cooling drum.

The gelatine bands stick less strongly to the cooling drum according to the invention and after the bands have been cooled to about 20° C. they may be easily removed from the cooling drum.

This results not only in a better, but also in a more uniform cooling of the gelatin bands. The preferred temperature of the coolant water, may be about 15 to 20° C., in comparison with from 20° C. to 22° C. for gelatin bands in the absence of 1,2-propyleneglycol. For example gelatin bands comprising 10% of such a component, e.g. 1,2-propyleneglycol (corresponding to Examples 1 and 3 hereinafter) preferred temperatures are from 18° C. to 20° C. and for gelatin bands comprising 21% of such a component (corresponding to Example 2) it is even lower, i.e. from 16° C. to 18° C.

The temperature of the cooling medium may be thermostatically controlled precisely e.g. with a cryostat.

The rate of flow of cooling medium, e.g. water, is conveniently from about 300 to 500 liters /hour. The rate may be conveniently controlled by a flow meter. The rate of flow may naturally be increased or decreased, for example with particularly thick or thin gelatine bands, or by increase or decrease of the rate of rotation of the cooling drum. Typically the rate of rotation of a cooling drum with a diameter of about 50 cm is about 0.5 rotations per minute.

The cooling medium, e.g. water, may be pumped in a single circuit, or preferably a double circuit as shown in the accompanying figure, through the cooling drum. By separation of the cooling medium into an upper and lower circuit an especially good and uniform cooling of the gelatine band may be obtained.

The cooling drum may be made of good conducting metal or metal alloy, e.g. aluminum or steel.

The disclosures of all the references mentioned above are incorporated by reference.

Hereinafter

Labrafil M 2125 CS is a transesterified ethoxylated vegetable oil known and commercially available under the trade name Labrafil which is obtained from corn oil and having an acid number of less than about 2, a saponification number of 155 to 175, an HLB value of 3 to 4, and an iodine number of 90 to 110. Cremophor RH 40 is a polyethyleneglycol-hydrogenated castor oil available under the trade name Cremophor RH 40, which has a saponification number of about 50 to 60, an acid number less than about 1, a water content (Fischer) less than about 2%, an $n_D^{60}$ of about 1.453 to 1.457 and an HLB of about 14 to 16.

Further details on the excipients are available in the literature such as H. Fiedler, Lexikon der Hilfsstoffe, $3^{rd}$ edition, vol 2, page 707, as well as manufacturer's brochures. The soft gelatin capsules according to the invention and the process for preparing same is further illustrated in the following Examples.

EXAMPLE 1

500 mg of a phospholipid solution containing 12% of 1,2-propyleneglycol as a solvent and diluent are encapsulated with a gelatin composition as follows:

| Component | |
|---|---|
| Gelatin | 47.5% |
| 1,2-Propyleneglycol | 10.0% |
| Glycerol | 6.0% |
| Water | 36.5% |
| | 100.0% |

After encapsulation and drying, the capsules are packaged in glass bottles. The capsules thus manufactured have a good capsule shape and may be stored for several years.

Comparative Example 1

500 mg of a phospholipid solution containing 12% of 1,2-propyleneglycol as a solvent and diluent are encapsulated with a gelatin composition as follows:

| Component | |
|---|---|
| Gelatin | 49.0% |
| Glycerol | 11.9% |
| Water | 39.1% |
| | 100.0% |

After encapsulation and drying, the capsules have deformations of the capsule shell so that they are not suitable for commercialization.

EXAMPLE 2 a) Microemulsion pre-concentrate comprising 1,2-propyleneglycol as the hydrophilic component for encapsulation in soft gelatin capsules:

| Component | Amount (mg/capsule) |
|---|---|
| 1,2-Propyleneglycol | 100.0 |
| Mono-, di- and triglycerides from corn oil | 160.0 |
| Cremophor ® RH 40 (1) | 190.0 |
| Cyclosporin A | 50.0 |
| Total amount | 500.0 |

(1) Cremophor® RH 40, is a polyoxyethylene-glycolated hydrogenated castor oil and a Trademark of the company BASF Ludwigshafen, Germany.

b) Gelatin composition containing 1,2-propyleneglycol as plasticizer for the encapsulation of the microemulsion pre-concentrate.

| Component | |
|---|---|
| Gelatin | 47.5% |
| 1,2-Propyleneglycol | 21.0% |
| Water | 31.5% |
| | 100.0% |

After the encapsulation of the microemulsion pre-concentrate the capsules are dried. After drying the capsules are packaged in moisture-tight glass bottles. The soft gelatin capsules thus prepared are stable for more than two years, e.g. more than 3 years, and have an unobjectionable appearance, i.e. a satisfactory capsule hardness and a satisfactory capsule shape.

The content analysis of 1,2-propyleneglycol in the microemulsion pre-concentrate and in the capsule shell exhibits the following values 2 days, 7 days, 18 days and 35 days after the encapsulation:

|  | Capsule contents | Capsule shell |  |
| --- | --- | --- | --- |
| Time | [mg] | [mg] | [%] |
| 2 days | 104.8 | 70.6 | 24.6 |
| 7 days | 107.3 | 72.0 | 25.8 |
| 18 days | 104.1 | 69.0 | 25.1 |
| 35 days | 101.5 | 70.7 | 25.7 |

The 1,2-propyleneglycol content in the capsule contents and in the capsule shell remains approximately constant over the whole test period, i.e. the composition of the microemulsion pre-concentrate is not changed.

EXAMPLE 3 a) Microemulsion pre-concentrate comprising 1,2-propyleneglycol as the hydrophilic component and ethanol as the co-solvent in the hydrophilic component for encapsulation in soft gelatin capsules:

| Component | Amount (mg/capsule) |
| --- | --- |
| 1,2-propyleneglycol | 150.0 |
| Ethanol | 150.0 |
| Mono-, di- and triglycerides from corn oil | 320.0 |
| Cremophor ® RH 40 (1) | 380.0 |
| Cyclosporin A | 100.0 |
|  | 1100.0 | b) Gelatin composition containing 1,2-propyleneglycol and glycerol as plasticizers for the encapsulation of the microemulsion pre-concentrate.

| Component |  |
| --- | --- |
| Gelatin | 47.5% |
| 1,2-Propyleneglycol | 10.0% |
| Glycerol | 6.0% |
| Water | 36.5% |
|  | 100.0% |

After the encapsulation of the microemulsion pre-concentrate the capsules are dried as in Example 2 and are packaged in glass bottles. The capsules thus prepared are stable for more than two years and have an unobjectionable appearance, i.e. a satisfactory capsule hardness and a satisfactory capsule shape.

The content analysis of 1,2-propyleneglycol in the microemulsion pre-concentrate and in the capsule shell exhibits the following values after 18 days and 42 days:

|  | Capsule contents | Capsule shell |  |
| --- | --- | --- | --- |
| Time | [mg] | [mg] |  |
| 18 days | 156.0 | 61.6 | 15.6 |
| 42 days | 152.4 | 60.8 | 15.4 |

Comparative Example 2 a) Microemulsion pre-concentrate comprising 1,2-propyleneglycol as the hydrophilic component for encapsulation in soft gelatin capsules:

| Component | Amount (mg/capsule) |
| --- | --- |
| 1,2-Propyleneglycol | 180.0 |
| Mono-, di- and triglycerides from corn oil | 360.0 |
| Cremophor ® RH 40 (1) | 360.0 |
| Cyclosporin A | 100.0 |
|  | 1000.0 | b) Gelatin composition containing glycerol as plasticizer for the encapsulation of the microemulsion pre-concentrate.

| Component |  |
| --- | --- |
| Gelatin | 49.0% |
| Glycerol | 11.9% |
| Water | 39.1% |
|  | 100.0% |

After the encapsulation of the microemulsion pre-concentrate the capsules are dried as in Examples 2 and 3 and are packaged in glass bottles. The capsules thus prepared are not stable. They have a deformed capsule shell which with increasing storage period becomes softer and more tacky so that the capsules are not any more suitable for commercial use.

The content analysis of 1,2-propyleneglycol in the microemulsion pre-concentrate and in the capsule shell exhibits the following values after 2 days, 7 days, 18 days and 56 days:

|  | Capsule contents | Capsule shell |  |
| --- | --- | --- | --- |
| Time | [mg] | [mg] | [%] |
| 2 days | 128.3 | 42.0 | 9.4 |
| 7 days | 120.5 | 50.7 | 11.8 |
| 18 days | 106.8 | 59.4 | 13.2 |
| 56 days | 100.2 | 74.2 | 16.3 |

The 1,2-propyleneglycol content in the capsule filling decreases with time, because the 1,2-propyleneglycol diffuses into the capsule shell. The change in the hydrophilic component leads to stability problems in the microemulsion pre-concentrate.

EXAMPLE 4 a) Microemulsion pre-concentrate comprising 1,2-propyleneglycol as the hydrophilic component and ethanol as the co-solvent in the hydrophilic component for encapsulation in soft gelatin capsules.

| Component | Amount (mg/capsule) |
|---|---|
| 1,2-Propyleneglycol | 35.0 |
| Ethanol | 75.0 |
| Mono, di- and triglycerides from corn oil | 172.0 |
| Cremophor ® RH 40 (1) | 202.5 |
| DL-alpha-Tocopherol | 0.5 |
| Cyclosporin A | 50.0 |
| | 535.0 | b) Gelatin composition containing 1,2-propyleneglycol and glycerol as plasticizers for the encapsulation of the microemulsion pre-concentrate.

| Component | Amount |
|---|---|
| Gelatin | 46.6% |
| 1,2-Propyleneglycol | 12.0% |
| Glycerol | 5.1% |
| Water | 35.3% |
| Titanium dioxide | 1.0% |
| | 100% |

After the encapsulation of the microemulsion pre-concentrate the capsules are dried. After drying the capsules are packaged in glass bottles. The capsules thus prepared are stable for more than three years and have an unobjectionable appearance, i.e. a satisfactory capsule hardness and a satisfactory capsule shape.

The content analysis of 1,2-propyleneglycol in the microemulsion pre-concentrate and in the capsule shell exhibits the following values after 7 days, 18 days and 35 days.

| Time | Capsule contents [mg] | Capsule shell [mg] | Capsule shell [%] |
|---|---|---|---|
| 7 days | 50.8 | 36.0 | 12.2 |
| 18 days | 51.5 | 33.4 | 11.6 |
| 35 days | 53.2 | 32.4 | 11.3 |

The 1,2-propyleneglycol content in the capsule fill increases after encapsulation especially in the first seven days. However the higher propyleneglycol content has no negative effect on the stability of the microemulsion pre-concentrate.

EXAMPLE 5 a) Microemulsion pre-concentrate comprising 1,2-propyleneglycol as the hydrophilic component and ethanol as the co-solvent in the hydrophilic component for encapsulation in soft gelatin capsules.

| Component | Amount (mg/capsule) |
|---|---|
| 1,2-Propyleneglycol | 37.5 |
| Ethanol | 75.0 |
| Labrafil M 2125 CS | 75.0 |
| Cremophor ® RH 40 (1) | 262.0 |
| DL-alpha-Tocopherol | 0.5 |
| [3'-desoxy-3'-oxo-MeBmt]$^1$-[Val]$^2$-Cyclosporin | 50.0 |
| | 500,0 | b) Gelatin composition containing 1,2-propyleneglycol and glycerol as plasticizers for the encapsulation of the microemulsion pre-concentrate.

| Component | Amount |
|---|---|
| Gelatin | 46,0% |
| 1,2-Propyleneglycol | 10.0% |
| Glycerol | 8.5% |
| Water | 35.5% |
| | 100.0% |

After the encapsulation of the microemulsion pre-concentrate the capsules are dried. After drying the capsules are packaged in glass bottles. The capsules thus prepared are stable for several years and have an unobjectionable appearance.

The content analysis of 1,2-propyleneglycol in the microemulsion pre-concentrate and in the capsule shell exhibits the following values after 2 days, 7 days, 18 days and 56 days.

| Time | Capsule contents [mg] | Capsule shell [mg] | Capsule shell [%] |
|---|---|---|---|
| 2 days | 48.5 | 31.6 | 11.1 |
| 7 days | 49.5 | 28.6 | 10.6 |
| 18 days | 49.4 | 26.6 | 10.4 |
| 56 days | 49.1 | 26.4 | 10.4 |

The 1,2-propyleneglycol content in the capsule fill increases after encapsulation especially in the first two days. However the microemulsion pre-concentrate remains stable on admixture with water.

EXAMPLE 6 a) Microemulsion pre-concentrate comprising 1,2-propyleneglycol as the hydrophilic component and ethanol as the co-solvent in the hydrophilic component for encapsulation in soft gelatin capsules.

| Component | Amount (mg/capsule) |
|---|---|
| 1,2-Propyleneglycol | 150.0 |
| Ethanol | 140.0 |
| Mono, di- and triglycerides from corn oil | 374.0 |
| Cremophor ® RH 40 (1) | 225.0 |
| DL-alpha-Tocopherol | 1.0 |
| Cyclosporin G | 100.0 |
| | 990.0 | b) Gelatin composition containing 1,2-propyleneglycol as plasticizer for the encapsulation of the microemulsion pre-concentrate.

| Component | Amount |
| --- | --- |
| Gelatin | 47.0% |
| 1,2-Propyleneglycol | 21.0% |
| Water | 32.0% |
|  | 100.0 |

After the encapsulation of the microemulsion pre-concentrate the capsules are dried. After drying the capsules are packaged in glass bottles. The capsules thus prepared are stable for several years and have an unobjectionable appearance.

The content analysis of 1,2-propyleneglycol in the microemulsion pre-concentrate and in the capsule shell exhibits the following values after 7 days, 18 days and 35 days.

| TIME | Capsule contents [mg] | Capsule shell [mg] | % |
| --- | --- | --- | --- |
| 7 days | 178.0 | 84.4 | 20.2 |
| 18 days | 171.7 | 91.2 | 21.2 |
| 35 days | 169.1 | 96.4 | 21.9 |

The 1,2-propyleneglycol content in the capsule fill increases after encapsulation in the first seven days. Afterwards the 1,2-propyleneglycol content in the capsule fill decreases slightly. However the microemulsion pre-concentrate remains sufficiently stable.

What is claimed is:

1. A soft gelatin capsule which comprises a shell and a liquid filling, wherein at the time of encapsulation said shell comprises gelatin and 1,2-propylene glycol and said filling comprises a rapamycin and 1,2-propylene glycol in a carrier medium therefor, wherein the shell, after drying, comprises 2–40% by weight 1,2-propylene glycol.

2. A capsule of claim 1 wherein the shell, after drying, comprises 5–40% 1,2-propylene glycol.

3. A capsule of claim 1 wherein the weight ratio of 1,2-propylene glycol to gelatin is 1:1 to 1:47.

4. A capsule of claim 3, wherein the ratio is from 1:1 to 1:4.

5. A capsule of claim 1, where the shell further comprises plasticizers and, optionally further auxiliary agents.

6. A capsule of claim 1, wherein the liquid filling further comprises a lipophilic component.

7. A capsule of claim 1, wherein the liquid filling further comprises a surfactant.

8. A capsule of claim 1, wherein the liquid filling forms an emulsion on mixing with water.

9. A capsule of claim 1, wherein the liquid filling is a microemulsion preconcentrate.

10. A capsule of claim 1, wherein the liquid filling further comprises ethanol.

11. A capsule of claim 1, wherein the shell, after drying, comprises 5–32% by weight 1,2-propylene glycol.

12. A capsule of claim 1, where the shell, after drying, comprises 10–32% by weight 1,2-propylene glycol.

13. A soft gelatin capsule which comprises a shell and a liquid filling, wherein at the time of encapsulation said shell comprises gelatin and 1,2-propylene glycol and said filling comprises 40-O-(2-hydroxy)ethyl rapamycin 1,2-propylene glycol in a carrier me therefor, wherein the shell, after drying, comprises 2–40% by weight 1,2-propylene glycol.

14. A capsule of claim 13 wherein the shell, after drying, comprises 5–40% 1,2-propylene glycol.

15. A capsule of claim 13 wherein the weight ratio of 1,2-propylene glycol to gelatin is 1:1 to 1:47.

16. A capsule of claim 15, wherein the ratio is from 1:1 to 1:4.

17. A capsule of claim 13, where the shell further comprises plasticizers and, optionally further auxiliary agents.

18. A capsule of claim 13, wherein the liquid filling further comprised a lipophilic component.

19. A capsule of claim 13, wherein the liquid filling further comprises a surfactant.

20. A capsule of claim 13, wherein the liquid filling forms an emulsion on mixing with water.

21. A capsule of claim 13, wherein the liquid filling is a microemulsion preconcentrate.

22. A capsule of claim, wherein the liquid filling further comprises ethanol.

23. A capsule of claim 13, wherein the shell, after drying, comprises 5–32% by weight 1,2-propylene glycol.

24. A capsule of claim 13, where the shell, after drying, comprises 10–32% by weight 1,2-propylene glycol.

25. A soft gelatin capsule which comprises a shell and a liquid filling, wherein at the time of encapsulation said shell comprises gelatin and 1,2-propylene glycol and said filling comprises a rapamycin and 1,2-propylene glycol in a carrier medium therefor, wherein said shell is produced from a gelatin composition comprising 1–35% by weight 1,2-propylene glycol.

26. A capsule of claim 25, further comprising glycerol in the shell at the time of encapsulation.

27. A capsule of claim 25, wherein the shell is produced from a gelatin composition comprising 4–30% by weight 1,2-propylene glycol.

28. A soft gelatin capsule which comprises a shell and a liquid filling, wherein at the time of encapsulation said shell comprises gelatin and 1,2-propylene glycol and said filling comprises rapamycin and 1,2-propylene glycol in a carrier medium therefor, wherein said shell is produced from a gelatin composition comprising 1–35% by weight 1,2-propylene glycol.

29. A capsule of claim 28, further comprising glycerol in the shell at the time of encapsulation.

30. A capsule of claim 28, wherein the shell is produced from a gelatin composition comprising 4–30% by weight 1,2-propylene glycol.

31. A soft gelatin capsule which comprises a shell and a liquid filling, wherein at the time of encapsulation said shell comprises gelatin and 1,2-propylene glycol and said filling comprises 40-O-(2-hydroxy)ethyl rapamycin and 1,2-propylene glycol in a carrier medium therefor, wherein said shell is produced from a gelatin composition comprising 1–35% by weight 1,2-propylene glycol.

32. A capsule of claim 31, further comprising glycerol in the shell at the time of encapsulation.

33. A capsule of claim 31, wherein the shell is produced from a gelatin composition comprising 4–30% by weight, 1,2-propylene glycol.

* * * * *

UNITED STATES PATENT AND TRADEMARK OFFICE
CERTIFICATE OF CORRECTION

PATENT NO.    : 6,555,132 B1
DATED         : April 29, 2003
INVENTOR(S)   : Brox et al.

It is certified that error appears in the above-identified patent and that said Letters Patent is hereby corrected as shown below:

<u>Column 14,</u>
Line 3, should read -- glycol in a carrier medium therefore, wherein the shell, after --.
Line 14, should read -- further comprises a lipophilic component. --.
Line 22, should read -- A capsule of claim 13, wherein the liquid filling further --.

Signed and Sealed this

Twenty-first Day of October, 2003

JAMES E. ROGAN
*Director of the United States Patent and Trademark Office*